United States Patent
Lelah

(10) Patent No.: US 12,076,299 B2
(45) Date of Patent: Sep. 3, 2024

(54) COMPOSITION AND METHOD TO ENHANCE COGNITIVE SUPPORT AND BRAIN HEALTH

(71) Applicant: Arjuna Natural PVT LTD, Aluva (IN)

(72) Inventor: Michael Lelah, Chicago, IL (US)

(73) Assignee: Arjuna Natural PVT LTD, Kerala (IN)

( * ) Notice: Subject to any disclaimer, the term of this patent is extended or adjusted under 35 U.S.C. 154(b) by 172 days.

(21) Appl. No.: 17/177,283

(22) Filed: Feb. 17, 2021

(65) Prior Publication Data

US 2021/0259990 A1    Aug. 26, 2021

Related U.S. Application Data

(60) Provisional application No. 62/979,067, filed on Feb. 20, 2020.

(51) Int. Cl.

| | | |
|---|---|---|
| A61K 31/055 | (2006.01) | |
| A23L 29/00 | (2016.01) | |
| A23L 33/105 | (2016.01) | |
| A23L 33/115 | (2016.01) | |
| A61K 9/00 | (2006.01) | |
| A61K 36/81 | (2006.01) | |
| A61K 47/14 | (2017.01) | |
| A61K 47/22 | (2006.01) | |
| A61K 47/26 | (2006.01) | |
| A61K 47/38 | (2006.01) | |
| A61K 47/46 | (2006.01) | |
| A61P 25/00 | (2006.01) | |

(52) U.S. Cl.
CPC .......... *A61K 31/055* (2013.01); *A23L 29/035* (2016.08); *A23L 33/105* (2016.08); *A23L 33/115* (2016.08); *A61K 9/0053* (2013.01); *A61K 36/81* (2013.01); *A61K 47/14* (2013.01); *A61K 47/22* (2013.01); *A61K 47/26* (2013.01); *A61K 47/38* (2013.01); *A61K 47/46* (2013.01); *A61P 25/00* (2018.01)

(58) Field of Classification Search
None
See application file for complete search history.

(56) References Cited

U.S. PATENT DOCUMENTS

| | | | |
|---|---|---|---|
| 10,183,053 B1 | 1/2019 | Rosen | |
| 2009/0297492 A1* | 12/2009 | Satoh | A61K 9/4858 424/754 |
| 2013/0034530 A1 | 2/2013 | Fantz | |
| 2013/0045183 A1* | 2/2013 | Gokaraju | A61K 36/28 424/769 |
| 2016/0192689 A1* | 7/2016 | Horn | A23L 33/22 424/93.46 |
| 2019/0015470 A1* | 1/2019 | Peng | A61P 17/18 |
| 2019/0167624 A1 | 6/2019 | Howard et al. | |
| 2019/0380984 A1 | 12/2019 | Bersohn | |

FOREIGN PATENT DOCUMENTS

| | | | |
|---|---|---|---|
| AU | 2019100842 A4 * | 9/2019 | |
| JP | 2011051942 | 3/2011 | |

OTHER PUBLICATIONS

Das et al. ("Potential of Glycowithanolides From *Withania somnifera* (Ashwagandha) as Therapeutic Agents for the Treatment of Alzheimer's Disease" World Journal of Pharmaceutical Research SJIF Impact Factor 5.990, vol. 4, Issue 6, 2015) (Year: 2015).*

Choudhary D., Bhattacharyya S., Bose S., "Efficacy and Safety of Ashwagandha (*Withania somnifera* (L.) Dunal) Root Extract in Improving Memory and Cognitive Functions," J Diet Suppl. Nov. 2, 2017;14(6):599-612.

Michael Lelah, Ph.D., "Lutein Esters are More Bioavailable than Free Lutein," NutriScience Innovations LLC, Trumbull, CT, USA, 2020.

Nuchi R. et al., "Effects of Lutein and Astaxanthin Intake on the Improvement of Cognitive Functions among Healthy Adults: A Systematic Review of Randomized Controlled Trials," Nutrients 2020, 12, 617, 1-24.

* cited by examiner

*Primary Examiner* — Robert A Wax
*Assistant Examiner* — Quanglong N Truong
(74) *Attorney, Agent, or Firm* — Stephen T. Scherrer; Monique A. Morneault; Scherrer Patent & Trademark Law, P.C.

(57) ABSTRACT

The present disclosure relates to relates to improved dietary supplement compositions formulated in a therapeutic effective amount for enhancing cognitive support and brain health. Specifically, the present disclosure relates to dietary and nutritional supplement compositions administered to a mammal in a therapeutically-effective amount to provide cognitive support and enhance overall brain health. The present disclosure further relates to a method of supporting cognitive health in a mammal comprising administering to the mammal in need thereof a therapeutically effective amount of a nutritional supplement comprising a combination of a carotenoid and an adaptogen.

14 Claims, No Drawings

COMPOSITION AND METHOD TO ENHANCE COGNITIVE SUPPORT AND BRAIN HEALTH

TECHNICAL FIELD

The present disclosure relates to compositions and methods for enhancing cognitive support and brain health. Specifically, the present disclosure relates to dietary and nutritional supplement compositions administered to a mammal in a therapeutically effective amount to provide cognitive support and enhance overall brain health. The present disclosure further relates to a method of supporting cognitive health in a mammal comprising administering to the mammal in need thereof a therapeutically effective amount of a nutritional supplement comprising a combination of lutein esters and ashwagandha extract.

BACKGROUND

We live in an aging society. Baby boomers, those born between 1946-1964 are the second largest age group, at an estimated 73 million. It is within this age group that people are concerned with and possibly dealing with the effects of aging, including changes relating to cognitive abilities. As people age, the brain naturally changes, affecting memory, learning, and other cognitive functions. Many older adults worry about losing cognitive abilities, including memory loss and the ability to learn and think as they age. Declining mental abilities, including the occurrence of Alzheimer's disease and dementia, are also becoming more and more of a concern as the population ages. Therefore, improving cognition, which is defined as the combination of several critical brain functions, including memory, judgment, language, intuition and the ability to learn, has come to the forefront of medicine and research. Research and development of new drugs to combat these signs of aging, including cognitive decline and brain health to hopefully slow down the aging process of the brain are at the forefront of the medical community. Additionally, cognitive health improvements and support may also be beneficial for school age children. And further, millennials who see the cognitive decline in their parents are looking for dietary solutions they can start now so as to have a beneficial effect in years to come.

In addition to traditional pharmaceuticals, there is also a growing interest in dietary or nutritional supplements and nutritional foods and beverages for the treatment of various health issues. More natural-based supplements, including gluten-free, vegetarian/vegan-based products, Non-GMO Project Verified, and Kosher & Halal certified are likewise entering the cognition support and brain health market.

For example, lutein is a carotenoid that has been shown to support vision health, and the combination of lutein and zeaxanthin are best known for eye health. However, more recently lutein and zeaxanthin have shown promise for cognitive health as well. Studies have shown that lutein and zeaxanthin can benefit all ages, from school age children to older adults. Ingredients geared toward gamers (avid video game players) have also been gaining popularity in the market. Gamers need both strong eyes and cognitive dexterity, lutein and lutein:zeaxanthin are becoming the choice ingredients for gamer support formulas. Applicant's product, Optilut® lutein esters and XanMax® free lutein: zeaxanthin complex dietary ingredients, have been designed to follow the cognitive health benefits.

Furthermore, there are initial indications that lutein esters, which is the form naturally available in plants, is more bioavailable than free lutein. See for example: https://cdn-.technologynetworks.com/ep/pdfs/lutein-esters-are-more-bioavailable-than-free-lutein.pdf, which is authored by the present inventor. Bioavailability is an important measure of the efficacy of dietary ingredients. Therefore, it would be anticipated that lutein esters are a preferred choice for cognitive support over free lutein.

*Withania somnifera* Dunal (WS) of family Solanaceae, known as Ashwagandha in Ayurveda, the ancient Hindu system of medicine, has been in use for centuries for treating various ailments. Ashwagandha is an adaptogen. Adaptogens mimic the body's own stress reducing hormones and increase the body's ability to recover from stress while creating an overall feeling of balance and normalization. Additionally, studies have shown than ashwagandha may be useful for improving memory and cognitive functions. See, Choudhary D., Bhattacharyya S., Bose S., *Efficacy and Safety of Ashwagandha (Withania somnifera (L.) Dunal) Root Extract in Improving Memory and Cognitive Functions*, J Diet Suppl. 2017 Nov. 2; 14(6): 599-612.

Additionally, there are numerous products in the market containing ashwagandha. One such product offered by the present Applicant is Shoden®, which is a clinically-tested, purified extract from the leaves and roots of the Ashwagandha plant. With an industry leading 35% Withanolide Glycosides (measured by HPLC), Shoden® offers high bioavailability and guaranteed activity even at low doses. Ashwagandha is believed to offer a variety of functions and benefits, including:

Sports & Performance—Improves energy, recovery and endurance; reduces fatigue and stress Sleep—Improves restful sleep, improved non-restorative sleep Weight management—Reduces stress-related appetite, helps balance blood sugar Stress—Reduces stress, supports the immune system Cognitive—Improves mind/body feeling, improves cognitive focus Fatigue—Increases resistance to fatigue, boosts energy, supports the immune system Vitality—Improves testosterone and dhea-s levels In view of the above, it would be desirable to provide a potent and therapeutically effective combination of ingredients, including a carotenoid, such as lutein or lutein esters, and an adaptogen, such as ashwagandha, in a pharmaceutical or nutraceutical composition having improved properties for supporting and enhancing cognitive functions and brain health. Additionally, it would be desirable to provide a method of supporting cognitive health in a mammal comprising administering to the mammal in need thereof a therapeutically effective amount of a nutritional supplement comprising a combination of free lutein or lutein esters and ashwagandha.

A need, therefore, exists for an improved dietary supplement composition formulated in a therapeutic effective amount to enhance and support cognitive functions and brain health in a variety of individuals, including those involved in video gaming, individuals concerned with cognitive health in the aging process, and those individuals wishing to enhance the learning experience. Specifically, a need exists for an improved dietary supplement composition formulated in a therapeutic effective amount to support overall cognitive health.

Moreover, a need exists for an improved dietary supplement composition formulated in a therapeutic effective amount to enhance, improve and support multiple aspects of cognitive skills.

A need further exists for an improved dietary supplement composition formulated in a therapeutic effective amount to support brain health through all ages.

A need further exists for an improved dietary supplement composition formulated using a combination of lutein and ashwagandha, which may have a synergistic effect on cognitive skills and brain health.

A need further exists for an improved dietary supplement composition formulated in a therapeutic effective amount to enhance, improve and support multiple aspects of cognitive skills without negative side effects.

SUMMARY

The present disclosure relates to improved dietary supplement compositions formulated in a therapeutic effective amount for enhancing cognitive skill and brain health. The composition is believed to produce a brain maintenance effect by shielding against the impact of aging on cognitive performance, as well as enhance various cognitive abilities for learning, gaming and brain health in general.

To this end, in an embodiment of the present disclosure, an improved dietary supplement composition formulated in a therapeutic effective amount to enhance overall cognitive health, is provided. The compositions comprise, in therapeutically effective amounts, a combination of a carotenoid and an adaptogen.

In one embodiment, an improved dietary supplement composition formulated in a therapeutic effective amount to enhance and maintain all aspects of cognitive function, is provided, wherein the composition is a combination of free lutein or lutein esters and ashwagandha extract, which when combined may have a synergistic effect on brain health.

In one embodiment of the present disclosure, an improved dietary supplement composition is provided for cognitive support and brain health having the following ingredients: about 10-80 mg per day lutein esters and about 60-600 mg per day ashwagandha extract, wherein the ashwagandha may be standardized to 35% glycowithanolides.

In another one embodiment of the present disclosure, an improved dietary supplement composition for use in connection with cognitive support and brain health is provided having the following ingredients: about 10-25 mg per day free lutein and about 60-120 mg per day ashwagandha extract, wherein the ashwagandha may be standardized to 35% glycowithanolides.

In one embodiment, an improved dietary supplement composition for use in connection with cognitive support and brain health is provided, wherein the composition comprises about 20 mg per day lutein esters and about 60 mg per day ashwagandha extract, wherein the ashwagandha is standardized may be 35% glycowithanolides.

In yet another embodiment, an improved dietary supplement composition for use in connection with cognitive support and brain health is provided, wherein the composition comprises about 40 mg per day lutein esters and about 60 mg per day ashwagandha extract, wherein the ashwagandha may be standardized to 35% glycowithanolides.

In one embodiment, an improved dietary supplement composition for use in connection with cognitive support and brain health is provided, wherein the composition comprises about 40 mg per day lutein esters and about 120 mg per day ashwagandha extract, wherein the ashwagandha may be standardized to 35% glycowithanolides.

In another embodiment, an improved dietary supplement composition formulated in a therapeutic effective amount to support cognitive health in connection with the aging process is provided.

In another embodiment, an improved dietary supplement composition formulated in a therapeutic effective amount to support cognitive skills to enhance video gaming skills is provided.

In another embodiment, a method of supporting cognitive health in a mammal is provided, comprising orally administering to the mammal in need thereof, a therapeutically effective amount of an improved dietary supplement composition formulated in a therapeutic effective amount to support cognitive skills and brain health, the composition comprising about 10-80 mg per day lutein esters and about 60-600 mg per day ashwagandha extract.

In yet another embodiment, a method of supporting cognitive health in a mammal is provided, comprising orally administering to the mammal in need thereof, a therapeutically effective amount of an improved dietary supplement composition formulated to support cognitive skills and brain health, wherein the composition is administered daily.

In yet another embodiment, it is an advantage and objective of the present disclosure to provide an improved dietary supplement composition formulated in a therapeutically effect amount to enhance cognitive skills and brain health in animals, particularly in pets such as cats, dogs, horses, etc. The dosages of ingredients would be ratioed depending in the weight of the particular animal. For example, the dosages above are for human use, with a reference human weight 100 kg. Thus, in comparison, for a 20 kg dog for example, the dosage may be ⅕ of the human dosages. Obviously, dosages may vary depending on species and weights and other factors, and thus the dosages recited herein are by example only.

It is, therefore, an advantage and objective of the present disclosure to provide an improved dietary supplement composition formulated in a therapeutic effective amount to enhance cognitive skills and brain health without negative side effects.

Yet another advantage and objective of the present disclosure to provide an improved dietary supplement composition formulated in a therapeutic effective amount to maintain cognitive skills and brain health during the aging process.

It is further an advantage and objective of the present disclosure to provide an improved dietary supplement composition formulated in a therapeutic effective amount to enhance performance of a gamer without negative side effects.

Additional features and advantages of the present disclosure are described in, and will be apparent from, the detailed description of the presently preferred embodiments.

DETAILED DESCRIPTION

The present disclosure relates to an improved dietary supplement composition formulated in a therapeutic effective amount to enhance cognitive skills and maintain brain health. The composition is believed to produce a brain maintenance effect by shielding against the impact of aging on cognitive performance, as well as potentially enhance cognitive abilities for memory enhancement, learning and gaming. The present disclosure relates to providing a formula for oral consumption, in the form of a dietary supplement. The ingredients used in the present composition are food or dietary ingredients, and do not include chemicals or drugs that are not suitable for human/animal consumption as foods or dietary supplements. The disclosure further relates to a method of supporting cognitive health in a mammal is provided, comprising orally administering to the mammal in need thereof, a therapeutically effective amount of an improved dietary supplement composition formulated to support cognitive skills and brain health, wherein the composition is administered daily.

It is a key embodiment of the present disclosure that the broad-spectrum compositions consist of dietary ingredients which have a positive effect on cognitive support and brain health. It is these particular functionalities that make the present dietary supplement composition unique. Additionally, it is a unique feature of the present composition to include ingredients that improve brain wave function, a physical manifestation of improved cognitive function, as well as improve neurotransmission, a chemical manifestation of improved cognitive function.

The first ingredient in the present composition is a carotenoid, which are generally in two categories-xanthophylls and carotenes. Xanthophylls include lutein, astaxanthin, zeaxanthin, etc. Lutein can be either free or ester forms. Naturally occurring lutein esters extracted from marigold flowers are not just one ester but a family of naturally occurring esters. They include mono- and di-esters. The main ester is lutein dipalmitate, but there are also smaller amounts of other esters such as palmitate, laurate, dilaurate, stearate, distearate, myristate and dimyristate esters. An extract of lutein esters may also include trans-zeaxanthin, a naturally occurring zeaxanthin.

In a preferred embodiment of the present disclosure, lutein esters are used, which as discussed above, has been shown to be more highly available than free ester. In a present composition, lutein esters are provided in a range of about 10-80 mg per day, which converts in a body to approximately 50% free lutein, with a free lutein range of 10-40 mg. In another embodiment of the present composition, lutein esters are provided in a range of about 20-50 mg per day, which converts in the body to approximately 50% free lutein, with a free lutein range of 10-25 mg. In another embodiment of the present composition, free lutein esters are provided in a range of about 10-25 mg per day, which coverts in the body to approximately 50% free lutein, with a free lutein range of 5-12.5 mg. As discussed above, there is new evidence that lutein plays a role in cognitive improvement, and therefore will work synergistically in the present formula.

The second ingredient of the present composition is an adaptogen, which improves brain health, reduces stress and anxiety, increases calm and relaxation, improves sleep ability, restores balance and improves physical performance. An adaptogen is an herb that has hormonal-like activity and protects the body against stress and other insults. Adaptogens are also known as phytohormones—i.e., plant extracts with hormonal-like activity. Adaptogens include but are not limited to rhodiola, ashwagandha, ginseng, astragalus, cordyceps, eleuthero, tulsi, turmeric, etc.

In the present composition, ashwagandha is the preferred adaptogen. Ashwagandha has the unique ability to help maintain homeostasis during intense stress, which is exactly what is needed by gamers to balance their performance. It is also believed that ashwagandha is useful for improving memory and cognitive functions, which are important attributes for the present composition. Ashwagandha is an Indian Ayurvedic herb also known as Indian ginseng, poison gooseberry, or winter cherry, and is also known by its Latin name *Withania somnifera*. Ashwagandha extract containing at least 5% withanolides (the bioactive components of Ashwagandha) with at least 35% glycowithanolides even more preferred. Preferred dosages for ashwagandha extract are between 60 mg and 600 mg per day, with more preferred dosages between 60 and 300 mg per day, with further preferred dosages between 60 and 120 mg per day. Ashwagandha extract bioavailability is high and effects can be felt within a few days making it a suitable selection for the present composition.

The present dietary supplement composition can be in any suitable delivery form including beadlets, pills (capsules, tablets, softgels, lozenges, chewables), gummies, powders for mixing to form beverages, ready to drink (RTD) beverages, or in foods such a snack bars, cookies or other food forms. Examples of compositions useful in the present disclosure include; lutein esters powders combined with ashwagandha extract powders; ashwagandha extract powder dispersed in lutein esters oil, with or without a dispersion agent; and, ashwagandha extract powder combined with encapsulated lutein esters oils.

In order to formulate these forms of oral consumables, there typically is the need to include inert ingredients. Inert ingredients do not perform any biological function, but instead help create the final form of the product suitable for consumption. Types of inert ingredients include fillers, coatings, lubrication aids, flow agents, binders, preservatives, flavors, fragrances, viscosity modifiers etc. The final product supplement, food or beverage may include any or all of these excipients as necessary to form the product, and it should be noted are not limited to these items listed.

In a most preferred embodiment, the delivery form of the present composition would be a unique single particle combination of the two ingredients, such as in a beadlet. This is a form distinct from a physical blend of the two ingredients. It is believed that the single particle combination product, which brings the two ingredients, for example lutein esters and ashwagandha extract-together in close proximity, results in a synergistic effect on cognitive health. Notwithstanding this preferred embodiment, other embodiments consisting of either a physical blend powders of the two ingredients, or combinations of oils and powders, are also preferred.

The present disclosure also relates to a method of supporting cognitive health in a mammal. "Mammal" may refer to humans, as well as, to animals and pets in particular. There is a growing market for supporting cognition and brain health in pets. A leading dog food manufacturer offers a senior dog food that is promoted as enhancing alertness and cognitive health in aging dogs. Therefore, the composition of the present disclosure may be offered in a therapeutically effect amount to enhance cognitive skills and brain health in animals, particularly pets such as cats, dogs, horses, etc. The dosages of ingredients would be ratioed depending in the weight of the particular animal. For example, the dosages described herein are generally designed for human use, with a reference human weight 100 kg. Thus, in comparison, for a 20 kg dog for example, the dosage is about ⅕ of the human dosages. Dosages and amounts of the present ingredients can be modified and changed to accommodate a variety of mammals.

EXAMPLES

The following are an explanation and results of usage trials utilizing combinations of the above ingredients in a dietary supplement useful for enhancing cognitive support and brain health. Studies were conducted to evaluate the effectiveness of the following formulations:

Formula 1: A dietary supplement formulation having 40 mg Opitlut® lutein esters and 60 mg Shoden® ashwagandha extract, was prepared. Formula 1 includes the following concentrations of ingredients: Ashwanganda: 20-22%; Lutein Esters concentrate: 17-21%; Modified food starch: 34-37%; Polysorbate: 3-5%; Acacia: 5-8%; Sugar: 2-4%; Fatty acid esters: 1-2%; and Tocopherols: 0.5%.

Beadlets of Formula 1 were prepared using known methods. Specifically, the ingredients were mixed together in a high shear mixer. The resulting wet mass is then fed into an extruder, and the extrudate is then fed into a spheronizer. The beadlets created in the spheronizer are then dried in a fluid bed drier.

Formula 2: A dietary supplement formulation having 40 mg Opitlut® lutein esters and 120 mg Shoden® ashwagandha extract, was prepared. Formula 2 includes the following concentration of ingredients: Ashwanganda: 33-35%; Lutein Esters concentrate: 14-18%; Modified food starch: 30-35%; Polysorbate: 3-5%; Acacia: 5-8%; Sugar: 2-4%; Fatty acid esters: 1-2%; and Tocopherols: 0.3%. Beadlets of Formula 2 were prepared using known methods as described above for Formula 1.

Formula 3—A dietary supplement formulation having 40 mg Opitlut® lutein esters and 60 mg Shoden® ashwagandha extract, was prepared. Formula 3 includes the following concentration of ingredients: Ashwanganda: 22%; Lutein Esters concentrate: 18%; Acacia: 20%; Microcrystalline cellulose: 25%; Sucrose 14.5%; and d-alpha Tocopherols: 0.5%. Beadlets of Formula 3 were prepared using known methods as described above for Formula 1.

Formula 4—A dietary supplement formulation having 40 mg Opitlut® lutein esters and 120 mg Shoden® ashwagandha extract, was prepared. Formula 4 includes the following concentration of ingredients: Ashwanganda: 35%; Lutein Esters concentrate: 15%; Acacia: 20%; Microcrystalline cellulose: 20%; Sucrose 9.5%; and d-alpha Tocopherols: 0.5%. Beadlets of Formula 3 were prepared using known methods as described above for Formula 1.

Trial Procedure and Data—In order to test the effects of the combination of ingredients on cognitive activity, two sets of experiments on mice were conducted. In the first set of experiments, test substances were administered orally to 8 animals in each group for 10 days. On the 10th day, the mice were evaluated for spatial learning by the T-Maze test, which is a simple maze used in animal cognition experiments. A risk assessment index was determined according to the formula-Risk Assessment Index=(frequency of tries)/(frequency of tries+Open Arm Entry). In the second set, the same procedure was used, however a pole climbing test was administered. The average of shock avoidance plus mistakes was determined (measured in seconds). For both sets of experiments, beadlets of Formula 3 and Formula 4 were tested, in addition to a placebo beadlet consisting of all the non-active ingredients in the formula (40% acacia, 40% microcrystalline cellulose, 19% sucrose, 1% d-alpha tocopherols). The results are shown in Table 1 below:

TABLE 1

| Treatment | Active Ingredients | Beadlet Human Dose (mg/day) | Beadlet Mouse Dose (mg/kg) | T-Maze test Risk Index (ave for 8 mice) | Pole Climbing test Avoidance/ mistakes (seconds) (ave for 8 mice) |
|---|---|---|---|---|---|
| Placebo | None | 300 | 61.5 | 12.9 | 12.8 |
| Formula 3 | Optilut 20 mg/ Shoden 60 mg | 300 | 61.5 | 16.4 | 11.0 |
| Formula 4 | Optilut 20 mg/ Shoden 120 mg | 360 | 73.8 | 18.0 | 7.9 |

The results show that cognitive abilities as measured by the T-Maze test and the Pole Climbing test improved with the combination of lutein and ashwagandha, and also improved with increasing dose of ashwagandha in the combination.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

I claim:

1. A dietary supplement composition comprising: a preservative a carotenoid comprising lutein/zeaxanthin or lutein esters and an adaptogen comprising ashwagandha extract formulated together in a therapeutic effective amount for enhancing cognitive skill and brain health.

2. The dietary supplement composition according to claim 1, wherein the ashwagandha extract is standardized to not less than 35% glycowithanolides.

3. A dietary supplement composition formulated in a therapeutic effective amount for enhancing cognitive skill and brain health, the composition comprising: a preservative about 10-80 mg lutein esters and about 60-600 mg ashwagandha extract.

4. The dietary supplement composition according to claim 3, wherein the composition comprises 40 mg lutein esters per day and 60 mg ashwagandha extract per day.

5. The dietary supplement composition according to claim 3, wherein the composition comprises 40 mg lutein esters per day and 120 mg ashwagandha extract per day.

6. The dietary supplement composition according to claim 3, wherein the composition comprises combining lutein esters powders and ashwagandha extract powders into a beadlet.

7. The dietary supplement composition according to claim 3, wherein the composition comprises a physical blend of lutein esters powders and ashwagandha extract powders.

8. The dietary supplement composition according to claim 3, wherein the composition comprises ashwagandha extract powder dispersed in a lutein esters oil.

9. The dietary supplement composition of claim 3 wherein the composition provides an immediate therapeutic effect to enhance cognitive performance.

10. The dietary supplement composition according to claim 3, wherein the composition is in a single or multiple combination of dosage pills, capsules, tablets, softgels, lozenges, powders, liquids, soft chews or gummies.

11. A method of supporting cognitive health in a mammal is provided, the method comprising:
orally administering to the mammal in need thereof a therapeutically effective amount of a composition comprising a preservative about 10-80 mg lutein esters and about 60-600 mg ashwagandha extract.

12. The method of claim 11, wherein the composition is formulated in a therapeutic effective amount to support cognitive skills and brain health.

13. The method of claim 11, wherein the method further includes administering the composition on a daily basis.

14. The method of claim 11, wherein the composition is administered in a dosage from about 10-80 mg per day lutein esters combined with about 60-600 mg per day ashwagandha extract.

* * * * *